United States Patent
Al-Khaldi et al.

(10) Patent No.: US 12,098,996 B2
(45) Date of Patent: Sep. 24, 2024

(54) APPARATUS FOR IN-SITU MONITORING OF GENERAL CORROSION AND LOCALIZED MICROBIOLOGICALLY INFLUENCED CORROSION (MIC)

(71) Applicant: Saudi Arabian Oil Company, Dhahran (SA)

(72) Inventors: Turki A. Al-Khaldi, Dammam (SA); Xiangyang Zhu, Dhahran (SA); Anas S. Rushaid, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 738 days.

(21) Appl. No.: 17/332,862

(22) Filed: May 27, 2021

(65) Prior Publication Data

US 2022/0381674 A1    Dec. 1, 2022

(51) Int. Cl.
| | |
|---|---|
| *G01N 17/04* | (2006.01) |
| *B01L 3/00* | (2006.01) |
| *C12M 1/34* | (2006.01) |
| *C12Q 1/02* | (2006.01) |
| *C12Q 1/18* | (2006.01) |

(52) U.S. Cl.
CPC ............ *G01N 17/04* (2013.01); *B01L 3/508* (2013.01); *C12M 41/46* (2013.01); *C12Q 1/025* (2013.01); *C12Q 1/18* (2013.01); *B01L 2300/0645* (2013.01)

(58) Field of Classification Search
None
See application file for complete search history.

(56) References Cited

U.S. PATENT DOCUMENTS

| | | |
|---|---|---|
| 6,946,855 B1 | 9/2005 | Hemblade |
| 6,960,288 B2 | 11/2005 | Marchal et al. |
| 7,282,928 B1 | 10/2007 | Hladky et al. |
| 7,686,938 B2 | 3/2010 | Gill et al. |
| 7,915,901 B2 | 3/2011 | Bell et al. |
| 8,506,777 B2 | 8/2013 | Hammonds et al. |

(Continued)

OTHER PUBLICATIONS

A. Legat, "Monitoring of steel corrosion in concrete by electrode arrays and electrical resistance probes" Electrochimica Acta 52(27): p. 7590-7598, Oct. 2007.*

(Continued)

*Primary Examiner* — J. Christopher Ball
(74) *Attorney, Agent, or Firm* — Leason Ellis LLP

(57) ABSTRACT

An apparatus for in-situ monitoring and measuring of general corrosion and localized microbiologically influenced corrosion (MIC) in a simulated environment is provided. The apparatus includes a chamber containing an electrolyte solution and a microbe specimen. The chamber includes a pair of electrical resistance (ER) probes that measure a current flowing through the electrolyte solution and a general corrosion rate on the surface of the ER probes. The chamber also includes a pair of electrochemical noise (EN) probes. The EN probes are aligned to face one another such that the EN probes measure a localized corrosion rate on the surface of the EN probes and measure the influence of gravity on MIC. The apparatus measures the general and localized corrosion rates simultaneously without polarizing the surface of the ER and EN probes.

17 Claims, 1 Drawing Sheet

(56) References Cited

U.S. PATENT DOCUMENTS

2010/0000879 A1   1/2010   Hladky et al.

OTHER PUBLICATIONS

A. M. Homborg, et al., "Detection of microbiologically influenced corrosion by electrochemical noise transients", Electrochimica Acta, 136: p. 223-232, Aug. 2014.*

A. Legat, et al., "Corrosion processes of steel in concrete characterized by means of electrochemical noise", Electrochimica Acta, 49(17-18): p. 2741-2751, Jul. 2004.*

Homborg, A. M., et al. "Detection of microbiologically influenced corrosion by electrochemical noise transients." Electrochimica acta 136 (2014): 223-232.

* cited by examiner

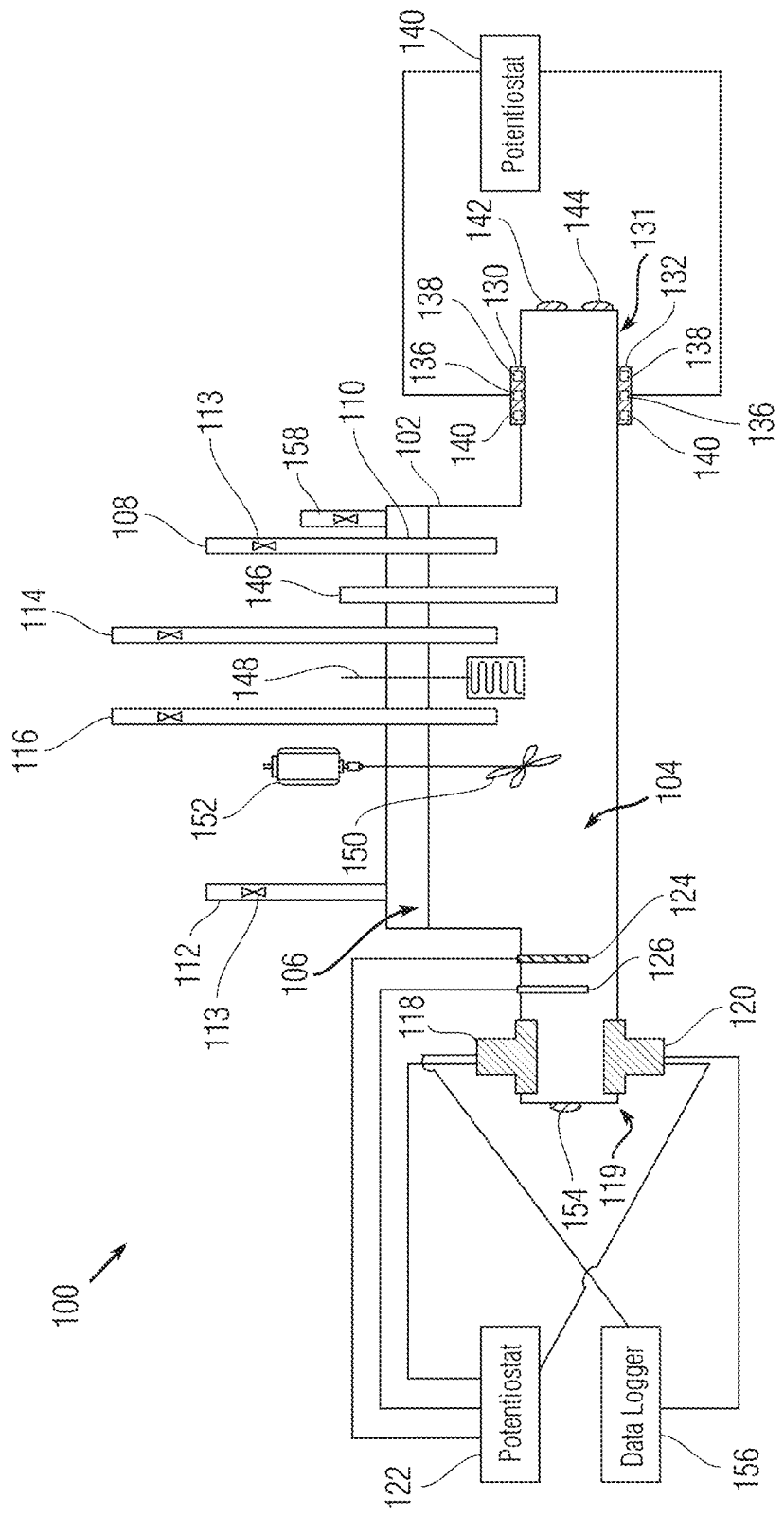

APPARATUS FOR IN-SITU MONITORING OF GENERAL CORROSION AND LOCALIZED MICROBIOLOGICALLY INFLUENCED CORROSION (MIC)

TECHNICAL FIELD

The present disclosure is generally related to monitoring of corrosion, including microbiologically influenced corrosion.

BACKGROUND OF THE DISCLOSURE

Corrosion, and in particular, microbiologically influenced corrosion (MIC) is a serious problem for equipment integrity in the oil and gas industry. Corrosions of all sorts, including MIC, can result in unplanned downtime and loss of efficiency, especially in water treatment systems. If left unchecked, MIC can require partial or complete replacement of system piping and components, or other costly repairs. For these reasons, monitoring of MIC in water treatment systems and other oil and gas facilities is essential and can result in cost savings.

Current techniques for monitoring MIC have limitations on the data that can be collected for evaluating the corrosivity of various microorganisms. For example, one conventional method for measuring MIC is the weight loss technique; however, the weight loss technique does not provide continuous monitoring. Certain electrochemical measurement techniques have also been used for MIC measurements, such as linear polarization resistance and electrochemical impedance spectroscopy. These electrochemical techniques are also limited in that they can disrupt the biofilm of the microbe due to surface polarization, which can result in lower corrosion rates measurement as compared with the actual corrosion rates. In addition, these electrochemical methods cannot measure localized corrosion.

Accordingly, there is a need for improved measurement tools for monitoring MIC. The present application addresses these and other challenges related to measuring and monitoring corrosion, and in particular, MIC.

SUMMARY OF THE DISCLOSURE

In a first aspect, an apparatus for in-situ monitoring and measuring of general corrosion and localized microbiologically influenced corrosion (MIC) in a simulated environment. The apparatus comprises a chamber containing an electrolyte solution and a microbe specimen. The chamber comprises a pair of electrical resistance (ER) probes mounted on top end and a bottom end, respectively, of a first side of the chamber. The pair of ER probes is configured to measure a current flowing through the electrolyte solution and a general corrosion rate on the surface of the ER probes. The chamber also comprises a first potentiostat operatively connected to the ER probes. The chamber also comprises a pair of electrochemical noise (EN) probes mounted on a top end and a bottom end, respectively, of a second side of the chamber. The pair of EN probes are aligned to face one another such that the pair of EN probes are configured to measure a localized corrosion rate on the surface of the EN probes and measure the influence of gravity on microbiologically influenced corrosion (MIC). The chamber also comprises a second potentiostat operatively connected to the EN probes. The apparatus is configured to measure the general corrosion rate and localized corrosion rate simultaneously without polarizing the surface of the ER probes and EN probes.

In another aspect, the two ER probes are aligned to face each other, such that ER probes configured to measure the influence of gravity on microbiologically influenced corrosion (MIC). In a further aspect, the location of the two ER probes is adjustable such that the distanced between the ER probes is altered. In another aspect, the orientation of the ER probes and the EN probes configures the apparatus to measure the influence of gravity on microbiologically influenced corrosion (MIC) in stagnant conditions.

In another aspect, the chamber further comprises a chemical injection port configured to inject one or more chemicals into the chamber. In a further aspect, the one or more chemicals are selected from the group consisting of biocides and corrosion inhibitors. In a further aspect, the apparatus is configured to monitor the effect of biocides or corrosion inhibitors on growth of the microbe specimen and the effect of biocides or corrosion inhibitors on the general and localized corrosion rates.

In another aspect, the chamber further comprises at least one of: an oxygen sensor, a pH sensor, a temperature sensor, a heating coil, and a solution stirrer.

In another aspect, the chamber further comprises a nitrogen gas pump configured to pump nitrogen gas to the electrolyte solution to simulate a microbe growth environment. In a further aspect, the chamber further comprises a nitrogen inlet operatively connected to the nitrogen gas pump and a nitrogen outlet.

In another aspect, the first potentiostat is operatively connected to a counter electrode and a reference electrode. In another aspect, the second potentiostat is operatively connected to a working electrode of each of the EN probes.

In another aspect, the apparatus further comprises a sampling port. In another aspect, the chamber comprises a gas phase and the electrolyte solution phase. In another aspect, the chamber further comprises a temperature probe configured to measure the temperature of the electrolyte solution.

In another aspect, the apparatus further comprises a data logger operatively connected the pair of ER probes. In another aspect, each of the EN probes further comprises a working electrode, a reference electrode, and a counter electrode.

BRIEF DESCRIPTION OF THE DRAWING FIGURES

FIG. 1 shows a diagram of an exemplary apparatus for in-situ monitoring and measuring of general corrosion and localized microbiologically influenced corrosion (MIC) in a simulated environment in accordance with one or more embodiments.

DETAILED DESCRIPTION OF CERTAIN EMBODIMENTS

By way of overview and introduction, the present application discloses an apparatus for in-situ monitoring and measuring of general corrosion (e.g., corrosion due to corrosivity of the environment) and localized microbiologically influenced corrosion (MIC) in a simulated environment. The apparatus of the present application also allows for the studying and monitoring of MIC in real time in a controlled environment by using the combination of ER and EN techniques to produce precise laboratory measurements based on short-term exposure.

More specifically, in accordance with one or more embodiments, the apparatus includes a chamber that holds an electrolyte solution (growth media). The chamber includes a microbial injection port for transferring a microbe specimen to the electrolyte solution. The chamber is also equipped with a pair of electrical resistance (ER) probes mounted on a top end and a bottom end, respectively, of one side of the chamber. The pair of ER probes is configured to measure a current flowing through the electrolyte solution and a general corrosion rate on the surface of the ER probes. A first potentiostat is operatively connected to the ER probes and can be configured to selectively allow surface polarization of the ER probes.

The chamber also includes a pair of electrochemical noise (EN) probes mounted on a top end and a bottom end, respectively, of the opposite side of the chamber. The EN probes are positioned facing one another, such that the pair of EN probes are configured to measure a localized corrosion rate on the surface of the EN probes and measure the influence of gravity on microbiologically influenced corrosion (MIC). A second potentiostat is operatively connected to the EN probes.

The present apparatus allows for simultaneous measurements of the general corrosion rate and the localized corrosion rate in a simulated environment without polarizing the surface of the EN probes. Moreover, the present apparatus allows for the monitoring of the extent of corrosion caused by microbes and the measurement of the corrosion rate simultaneously. Additionally, in certain embodiments, the present apparatus can be utilized to study the effectiveness of both corrosion inhibitor and biocide in mitigation of corrosion which originates either from microbial activities or due to corrosivity of the environment These and other aspects of the present apparatus are described in further detail below with reference to the accompany drawing FIGURE, in which one or more illustrated embodiments and/or arrangements of the corrosion inhibitors are shown. The apparatus of the present application is not limited in any way to the illustrated embodiments and/or arrangements. It should be understood that the apparatus as shown in the accompanying FIGURE is merely exemplary of the apparatuses of the present application, which can be embodied in various forms as appreciated by one skilled in the art. Therefore, it is to be understood that any structural and functional details disclosed herein are not to be interpreted as limiting the present apparatus, but rather are provided as a representative embodiment and/or arrangement for teaching one skilled in the art one or more ways to implement the present apparatus.

FIG. 1 displays an apparatus 100 for in-situ monitoring and measuring of general corrosion and localized microbiologically influenced corrosion (MIC) in a simulated environment in accordance with one or more embodiments. With reference now to FIG. 1, the apparatus 100 comprises a chamber 102 for housing the simulated environment. In general, the chamber 102 is made of one or more non-corrosive materials, preferably non-corrosive materials that are transparent. For example, in one or more embodiments, the chamber 102 is a clear glass chamber. The chamber 102 is sized and shaped to hold an electrolyte solution 104, which is a growth media for one or microbes (e.g., bacteria). In or more embodiments, the electrolyte solution 104 is a growth media that simulates field condition at ambient or low pressure. In at least one embodiment, the solution 104 can be a collected sample from a field operation containing actual bacteria from petroleum reservoirs, such as sulfide reducing bacteria (SRB). However, in other embodiments, other types of growth media can be used to investigate the corrosivity of those types of growth media. In operation, as shown in FIG. 1, a lower portion of the chamber 102 holds the electrolyte solution 104 (liquid phase), and an upper portion of the chamber 102 holds a gas phase 106.

In one or more embodiments, the gas phase 106 is comprised of nitrogen gas. In such embodiments, a nitrogen gas pump 108 pumps the nitrogen into the chamber 102 via a nitrogen inlet 110. The chamber 102 can also comprise a nitrogen outlet 112 configured to remove a portion of the nitrogen gas during operation. In one or more embodiments, each of the nitrogen inlet 110 and nitrogen outlet 112 can comprise a valve 111 and 113, respectively, for controlling the volume of nitrogen gas entering and exiting the chamber 102. The introduction of nitrogen into the chamber 102 along with the electrolyte solution 104 simulate a microbe growth environment.

With continued reference to FIG. 1, the chamber 102 further includes a microbial injection port 114. The microbial injection port is configured to transfer a microbe specimen to the electrolyte solution in the chamber 102. In one or more embodiments, the chamber 102 can also include a chemical injection port 116, which is configured to transfer one or more chemicals to the chamber 102, such as corrosion inhibitors and biocides. In at least one embodiment, when chemicals such as corrosion inhibitors or biocides are introduced into the chamber 102, the apparatus 100 can be configured to monitor the effect of the corrosion inhibitor or the biocide on growth of the microbe specimen and the effect of the corrosion inhibitor or the biocide on the general and localized corrosion rates. This monitoring can be accomplished via the readings of one or more sensors of the apparatus 100, such as the sensors mentioned in further detail below. While the microbial injection port 114 and the chemical injection port 116 are shown as separate ports in the exemplary embodiment of FIG. 1, in at least one embodiment, a single port can be used for microbial injection and chemical injection into the chamber 102.

The chamber 102 further includes a pair of electrical resistance (ER) probes 118 and 120. The ER probes 118 and 120 are mounted on a top end and a bottom end, respectively, of a first side 119 of the chamber 120. As such, as shown in FIG. 1, the surface (outer surface) of each ER probe 118 and 120 is in contact with the electrolyte solution (and the microbe sample) in the chamber 102. The pair of ER probes 118, 120 is configured to measure a current flowing through the electrolyte solution and a general corrosion rate on the surface of the ER probes 118 and 120.

In one or more embodiments, as exemplified in the embodiment shown in FIG. 1, the two ER probes 118, 120 are aligned in the chamber 102 and facing each other (e.g., ER probe 118 in the "12 o'clock position" and the ER probe 120 in the "6 o'clock position"). In this alignment, the ER probes 118 and 120 are configured to measure the influence of gravity on microbiologically influenced corrosion (MIC), particularly in stagnant conditions. Specifically, as the microbe is allowed to grow in the electrolyte solution (growth media), a biofilm is formed a surface of the ER probes 118 and 120. As such, the ER probes in this alignment can measure the gravitational effect on biofilm formation on the surface of the ER probes 118 and 120. Specifically, in one or more embodiments, as shown in FIG. 1, the ER probes 118 and 120 are located in the "12 o'clock position" and the "6 o'clock position," respectively. Each ER probe provides the corrosivity date according to their position. Gravity can have an effect on MIC, such as the present nutrition or formation of microbial colonies. For example, the required nutrients can sometimes fall under the weight of the microbial colonies and in interaction with the gravitational force, such that the nutrients are found more on the surfaces than in the bulk solution. In at least one embodiment, the locations of the two ER probes 118 and 120 is adjustable such that the distanced between the ER probes 118 and 120 is altered. Adjustments of the distance between the ER probes 118 and 120, allows the apparatus 102 to have better simulation or study dilution factor on MIC corrosion.

The pair of ER probes 118, 120 are operatively connected to a first potentiostat 122. In at least one embodiment, the first potentiostat 122 can be configured to selectively cause surface polarization of the ER probes 118 and 120. As such, in one or more embodiments, the first potentiostat 122 enables the apparatus to selectively monitor the influence of surface polarization on corrosion, such as in case of applying cathodic protection on MIC. The ER probes 118 and 120 can each comprises a sensing element that is connected to the first potentiostat 122. The first potentiostat 122 is also connected to a counter electrode 124 and a reference electrode 126, which are located within the chamber 102 adjacent to the ER probe 118.

In one or more embodiments, the ER probes 118, 120 can be comprised of a corroding metal such that the ER probes 118, 120 are configured to measure the general rate of corrosion from the injected microbe on a surface of the corroding metal. For example, the ER probes 118, 120 can be comprised of the same metal as a structure in a water treatment facility, such that the ER probes measure the general corrosion rate of the microbe on a simulated environment of the water treatment facility. In one or more embodiments, the corroding metal can be any type of metal. In at least one embodiment, the corroding metal can comprise carbon steel or stainless steel. In one or more embodiments, the ER probes 118, 120 are used to determine the metal loss on the probe due to corrosion, and the amount of metal loss is used to determine a general corrosion rate.

The chamber 102 further includes a pair of electrochemical noise (EN) probes 130 and 132. In one or more embodiments, the EN probes 130 and 132 are mounted on a top end and a bottom end, respectively, of a second side 131 of the chamber and positioned facing one another, such that a surface (outer surface) of each EN probe 130, 132 is in contact with the electrolyte solution (growth media) and the sample microbe. Thus, as the microbe is allowed to grow in the electrolyte solution (growth media), a biofilm is formed a surface of the EN probes 130 and 132.

Due to their orientation, the pair of EN probes 130 and 132 are configured to measure a localized corrosion rate on the surface of the EN probes 130 and 132 and measure the influence of gravity on microbiologically influenced corrosion (MIC), particularly in stagnant conditions. In other words, because of the location and alignment of the EN probes 130 and 132, the EN probes 130 and 132 can measure the gravitational effect on the MIC (biofilm) formed on the surface of the EN probes 130 and 132.

This electrochemical noise (EN) technique monitors the fluctuations of the electrode potential, or the galvanic current of a metal in a function of time. EN analysis of the frequencies of the signals provides indications of the active type of corrosion by making a particular distinction between uniform corrosion and localized corrosion. Thus, the EN probes 130 and 132 are particularly effective for detecting and quantifying localized corrosion. On the other hand, the electrical resistance (ER) probes 118 and 120 can provide a general corrosion rate, which is calculated from the thickness reduction (metal loss) of the metal on the probe; however, its response to localized corrosion is limited. Specifically, the ER probes 118 and 120 measure the metal loss that is correlated to the generalized corrosion rate, as an increase in electrical resistance over time in the probe sensing element. The increase in electrical resistance is proportional to the accumulated corrosion of the probe element over the exposure period.

The pair of EN probes 130, 132 are operatively connected to a second potentiostat 134. The second potentiostat 134 is operatively connected to a working electrode 136, a counter electrode 138, and a reference electrode 140 at each of the EN probes 130 and 132. The second potentiostat 134 measures the current flow between the working electrode 136 and the counter electrode 138.

By simultaneously operating the pair of ER probes 118, 120 and the pair of EN probes 130, 132, the apparatus 100 can be configured to measure the general corrosion rate and localized corrosion rate, respectively, in a simultaneous fashion without polarizing the surface of the ER probes 118 and 120 or the EN probes 130 and 132.

With continued reference to FIG. 1, in one or more embodiments, the chamber 102 can further comprise additional features, such an oxygen sensor 142, a pH sensor 144, and a temperature sensor 146. The oxygen sensor 142, pH sensor 144, and temperature sensor 146 can be used to measure and monitor the oxygen levels, the pH, and the temperature, respectively, of the electrolyte solution 104 in the chamber 102 to ensure that the environment in the chamber 102 adequately mimics the microbe growth and corrosion environment of the equipment that the apparatus 100 is simulating (e.g., water treatment facility).

In one more or embodiments, the chamber 102 can further include a heating coil 148 and a solution stirrer 150. The heating coil 148 is in contact with the electrolyte solution 104 and is used to alter the temperature of the electrolyte solution 104 such that the electrolyte solution 104 sufficiently simulates the desired microbe growth environment. Similarly, the solution stirrer 150 is used to selectively stir the electrolyte solution 104 to further simulates a microbe growth environment, such as a water treatment facility. In one or more embodiments, the solution stirrer 150 can be operatively connected to a stirrer motor 152, which is configured to mechanically cause the solution stirrer 150 to spin.

In one or more embodiments, the chamber 102 also includes a sampling port 154, at which samples of the electrolyte solution and microbe specimen can be retrieved for further testing. In at least one embodiment, the apparatus 100 can further include at least one data logger 156. The data logger 156 can comprise a microprocessor and can be configured to record data over time. For example, as shown in FIG. 1, the data logger 156 can be operatively connected to the ER probes 118 and 120 such that the data logger can record data from the ER probes over time. In one or more embodiments, a data logger can also be operatively connected to the EN probes 130 and 132 for recording data from the EN probes over time. In one or more embodiments, the chamber 102 can further include a filling port 158 for filling the chamber with the electrolyte solution 104 (growth media).

Overall, the present apparatus provides several advantages over conventional apparatuses and methods for monitoring MIC. Specifically, the present apparatus allows for in-situ measuring and monitoring of general corrosion and localized microbial corrosion simultaneously in a simulated environment. Furthermore, the present apparatus can be utilized to study the effectiveness of both corrosion inhibitor and biocide in mitigating corrosion that originates either from microbial activities or due to corrosivity of the environment taking into consideration the influence of gravity and the influence of surface polarization (cathodic protection). These advantages are achieved, in part, by the apparatus' simultaneous use of EN techniques to measure localized corrosion rates and ER techniques to measure general corrosion rates. Advantageously, both the EN and ER probes of the present apparatus do not require any surface polarization of the probes to measure the corrosion activities, which minimize the disturbance of the surface of the probes, and thus minimizes disturbance of microbial activities on the surface of the probes. However, the influence of surface polarization such in case of applying cathodic protection can be selectively studied by the present apparatus via polarization of the ER probes through its connection to the potentiostat.

Although much of the foregoing description has been directed to an apparatus for in-situ monitoring and measuring of general corrosion and localized MIC in a simulated environment, the apparatus disclosed herein can be similarly deployed and/or implemented in scenarios, situations, and settings far beyond the referenced scenarios. It should be further understood that any such implementation and/or deployment is within the scope of the apparatus described herein.

It is to be further understood that like numerals in the drawing represent like elements through the FIGURE, and that not all components and/or steps described and illustrated with reference to the FIGURE are required for all embodiments or arrangements. Further, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "including," "comprising," or "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Notably, the FIGURE and examples above are not meant to limit the scope of the present disclosure to a single implementation, as other implementations are possible by way of interchange of some or all the described or illustrated elements. Moreover, where certain elements of the present disclosure can be partially or fully implemented using known components, only those portions of such known components that are necessary for an understanding of the present disclosure are described, and detailed descriptions of other portions of such known components are omitted so as not to obscure the disclosure. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present disclosure encompasses present and future known equivalents to the known components referred to herein by way of illustration.

The foregoing description of the specific implementations will so fully reveal the general nature of the disclosure that others can, by applying knowledge within the skill of the relevant art(s), readily modify and/or adapt for various applications such specific implementations, without undue experimentation, without departing from the general concept of the present disclosure. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings are shown accordingly to one example and other dimensions can be used without departing from the disclosure.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

What is claimed is:

1. An apparatus for in-situ monitoring and measuring of general corrosion and localized microbiologically influenced corrosion (MIC) in a simulated environment, comprising:
   a chamber containing an electrolyte solution and a microbe specimen, wherein the chamber comprises:
   a pair of electrical resistance (ER) probes mounted on a top end and a bottom end, respectively, of a first side of the chamber, wherein the pair of ER probes is configured to measure a current flowing through the electrolyte solution and a general corrosion rate on the surface of the ER probes;
   a first potentiostat operatively connected to the ER probes;
   a pair of electrochemical noise (EN) probes mounted on a top end and a bottom end, respectively, of a second side of the chamber, wherein the pair of EN probes are aligned to face one another such that the pair of EN probes are configured to measure a localized corrosion rate on the surface of the EN probes and measure the influence of gravity on microbiologically influenced corrosion (MIC); and
   a second potentiostat operatively connected to the EN probes,
   wherein the apparatus is configured to measure the general corrosion rate and localized corrosion rate simultaneously without polarizing the surface of the ER probes and EN probes.

2. The apparatus of claim 1, wherein the two ER probes are aligned to face each other, such that the ER probes are configured to measure the influence of gravity on microbiologically influenced corrosion (MIC).

3. The apparatus of claim 2, wherein the location of the two ER probes is adjustable such that the distance between the ER probes is altered.

4. The apparatus of claim 2, wherein the orientation of the ER probes and the EN probes configures the apparatus to measure the influence of gravity on microbiologically influenced corrosion (MIC) in stagnant conditions.

5. The apparatus of claim 1, wherein the chamber further comprises a chemical injection port configured to inject one or more chemicals into the chamber.

6. The apparatus of claim 5, wherein the one or more chemicals are selected from the group consisting of biocides and corrosion inhibitors.

7. The apparatus of claim 6, wherein the apparatus is configured to monitor the effect of biocides or corrosion inhibitors on growth of the microbe specimen and the effect of biocides or corrosion inhibitors on the general and localized corrosion rates.

8. The apparatus of claim 1, wherein the chamber further comprises at least one of:
    an oxygen sensor, a pH sensor, a temperature sensor, a heating coil, and a solution stirrer.

9. The apparatus of claim 1, wherein the chamber further comprises a nitrogen gas pump configured to pump nitrogen gas to the electrolyte solution to simulate a microbe growth environment.

10. The apparatus of claim 9, wherein the chamber further comprises a nitrogen inlet operatively connected to the nitrogen gas pump and a nitrogen outlet.

11. The apparatus of claim 1, wherein the first potentiostat is operatively connected to a counter electrode and a reference electrode.

12. The apparatus of claim 1, wherein the second potentiostat is operatively connected to a working electrode of each of the EN probes.

13. The apparatus of claim 1, further comprising a sampling port.

14. The apparatus of claim 1, wherein the chamber comprises a gas phase and the electrolyte solution phase.

15. The apparatus of claim 1, wherein the chamber further comprises a temperature probe configured to measure the temperature of the electrolyte solution.

16. The apparatus of claim 1, further comprising a data logger operatively connected the pair of ER probes.

17. The apparatus of claim 1, wherein each of the EN probes further comprises a working electrode, a reference electrode, and a counter electrode.

* * * * *